(12) United States Patent
Morrison et al.

(10) Patent No.: US 7,270,665 B2
(45) Date of Patent: Sep. 18, 2007

(54) VARIABLE OFFSET SPINAL FIXATION SYSTEM

(75) Inventors: Matthew M. Morrison, Cordova, TN (US); Douglas N. Baker, Germantown, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 541 days.

(21) Appl. No.: 10/459,628

(22) Filed: Jun. 11, 2003

(65) Prior Publication Data

US 2004/0254574 A1 Dec. 16, 2004

(51) Int. Cl.
*A61B 17/56* (2006.01)
*A61B 17/58* (2006.01)

(52) U.S. Cl. .......................................... 606/61; 606/73

(58) Field of Classification Search .................. 606/60, 606/61, 72, 73, 71
See application file for complete search history.

(56) References Cited

U.S. PATENT DOCUMENTS

| | | | |
|---|---|---|---|
| 4,569,338 A | 2/1986 | Edwards |
| 4,827,918 A | 5/1989 | Olerud |
| 5,047,029 A | 9/1991 | Aebi |
| 5,053,034 A | 10/1991 | Olerud |
| 5,176,680 A | 1/1993 | Vignaud |
| 5,254,118 A | 10/1993 | Mirkovic |
| 5,261,909 A | 11/1993 | Sutterlin et al. |
| 5,423,818 A | 6/1995 | Van Hoeck et al. |
| 5,527,314 A | 6/1996 | Brumfield |
| 5,534,002 A | 7/1996 | Brumfield |
| 5,562,662 A | 10/1996 | Brumfield |
| 5,643,259 A | 7/1997 | Sasso et al. |
| 5,643,263 A | 7/1997 | Simonson |
| 5,643,264 A | 7/1997 | Sherman et al. |
| 5,645,544 A | 7/1997 | Tai et al. |
| 5,885,285 A | 3/1999 | Simonson |
| 5,938,663 A | 8/1999 | Petreto |
| 5,947,967 A | 9/1999 | Barker |
| 5,976,135 A | 11/1999 | Sherman et al. |
| 5,980,521 A | 11/1999 | Montague et al. |
| 6,183,473 B1 | 2/2001 | Ashman |
| 6,210,413 B1 | 4/2001 | Justis |
| 6,248,107 B1 | 6/2001 | Foley |
| 6,402,749 B1 | 6/2002 | Ashman |
| 6,471,703 B1 | 10/2002 | Ashman |
| 6,520,962 B1 | 2/2003 | Taylor |
| 6,562,038 B1 | 5/2003 | Morrison |
| 6,569,164 B1 * | 5/2003 | Assaker et al. ............... 606/61 |
| 6,572,618 B1 | 6/2003 | Morrison |
| 6,579,292 B2 | 6/2003 | Taylor |

(Continued)

*Primary Examiner*—Pedro Philogene
(74) *Attorney, Agent, or Firm*—Woodard, Emhardt, Moriarty, McNett & Henry LLP (57) ABSTRACT

A bone fixation system for locking a longitudinal member, such as a spinal rod, to a bone anchor element allowing a variable orientation of the axis of the longitudinal member relative to the axis of the bone anchor. A one-piece body element split along a substantially horizontal plane into upper and lower portions by a slot includes a ball element through which a longitudinal member, such as a spinal rod, may pass. A portion of a bone anchor element passes through an aperture having portions on each of the upper and lower portions of the body element. Tightening a set screw draws the upper and lower portions of the body element together and locks the bone anchor and spinal rod into the desired position.

41 Claims, 7 Drawing Sheets

U.S. PATENT DOCUMENTS 6,626,906 B1 9/2003 Young
6,685,705 B1 2/2004 Taylor

2002/0068938 A1 * 6/2002 Jackson .................. 606/61

* cited by examiner

Fig. 13

VARIABLE OFFSET SPINAL FIXATION SYSTEM

FIELD OF THE INVENTION

The present invention relates generally to medical implants and more particularly to a receiving and locking assembly adapted to connect a longitudinal member such as a rod to a bone anchor.

BACKGROUND OF THE INVENTION

There are numerous known medical implants for the treatment of various bone injuries, deformities and disorders. Among these medical implants are spinal fixation systems implanted during a surgical procedure to treat a variety of problems. These treatments include correction of congenital spinal deformities, repair of spinal injuries and fusion of vertebrae to stabilize degenerative conditions and alleviate chronic lower back pain. Several techniques and systems have been developed for correcting and/or stabilizing the spine and/or facilitating spinal fusion. In one type of system, a longitudinal member, such as a bendable rod, is disposed along a portion of the vertebral column, and is fixed to two or more vertebrae along the length of the column by way of a number of fixation elements. Such vertebral fixation elements can include hooks, screws or bolts of various types, each of which are configured to engage specific portions of the vertebral body. In one example, a surgeon can first attach the vertebral fixation elements to the spine in appropriate anatomic positions, and then connect each vertebral fixation element to the spinal rod. Some fixation elements include a head adapted to receive a rod or other longitudinal member. In other systems, a receiving and locking assembly is used to rigidly connect a rod to a fixation element.

U.S. Pat. No. 5,176,680 discloses a device for fixing a spinal rod to vertebral screws. The spinal rod is passed through a split ring which is positioned between the prongs of a vertebral screw having a forked head. The assembly is locked into the desired position by a locking screw threaded between the prongs which and directly onto the split ring.

An assembly for fixing a spinal rod to a bone bolt is shown in U.S. Pat. No. 5,938,663. The spinal rod is passed through a split ring which is disposed within a clamp of a locking assembly. The threaded head of the bolt passes through a pair of openings in the locking assembly and a locking nut is threaded onto the bolt. As the locking nut is tightened, the locking assembly is sandwiched at a particular location between the locking nut and a medial flange or head on the bolt.

SUMMARY OF INVENTION

The invention is set forth in the claims below, and the following is not in any way to limit, define or otherwise establish the scope of legal protection. In general terms, the present invention relates to an orthopedic apparatus for locking a longitudinal member to a bone anchor member. One embodiment of the present invention relates to an orthopedic apparatus including a bone anchor member having an anchor portion and a shaft portion, a locking assembly having a body member and a compressible ring, and a set screw. The body member includes a lower portion and an upper portion linked by a connecting portion and separated by a slot. The lower portion and the upper portion each include a first aperture and a second aperture. The first aperture is configured such that the shaft portion of the bone anchor member can be passed there through. The second aperture is configured such that the set screw may be threaded therethrough so as to compress the body member. The body member further includes a cavity within the connecting portion, upper portion and lower portion. The compressible ring includes a central passage to receive the longitudinal member and is housed by the body member cavity. Compression of the body member by the set screw locks the compressible ring and longitudinal member in the desired position.

DESCRIPTION OF THE PREFERRED EMBODIMENTS

For the purposes of promoting understanding of the principles of the invention, reference will now be made to the embodiments illustrated in the drawings and specific language will be used to describe the same. It will nevertheless be understood that no limitation of the scope of the invention is hereby intended and alterations and modifications in the illustrated device, and further applications of the principles of the present invention as illustrated herein being contemplated, as would normally occur to one skilled in the art to which the invention relates.

Referring first generally to FIGS. 1, 2, 3, and 13, there is shown an orthopedic apparatus 20 according to one embodiment of the present invention. Orthopedic apparatus 20 includes a pedicle screw 22, a spinal rod 24, and a locking assembly 26 comprising a body member 28 and a compressible ring 30. Pedicle screw 22 connects to body member 28 substantially along a first axis, and rod 24 fits within ring 30 inside body member 28, allowing rod 24 to extend along any of a number of second axes, as further described below. A set screw 32 is provided for compression of locking assembly 26, also as described below.

Figures 1, 2:
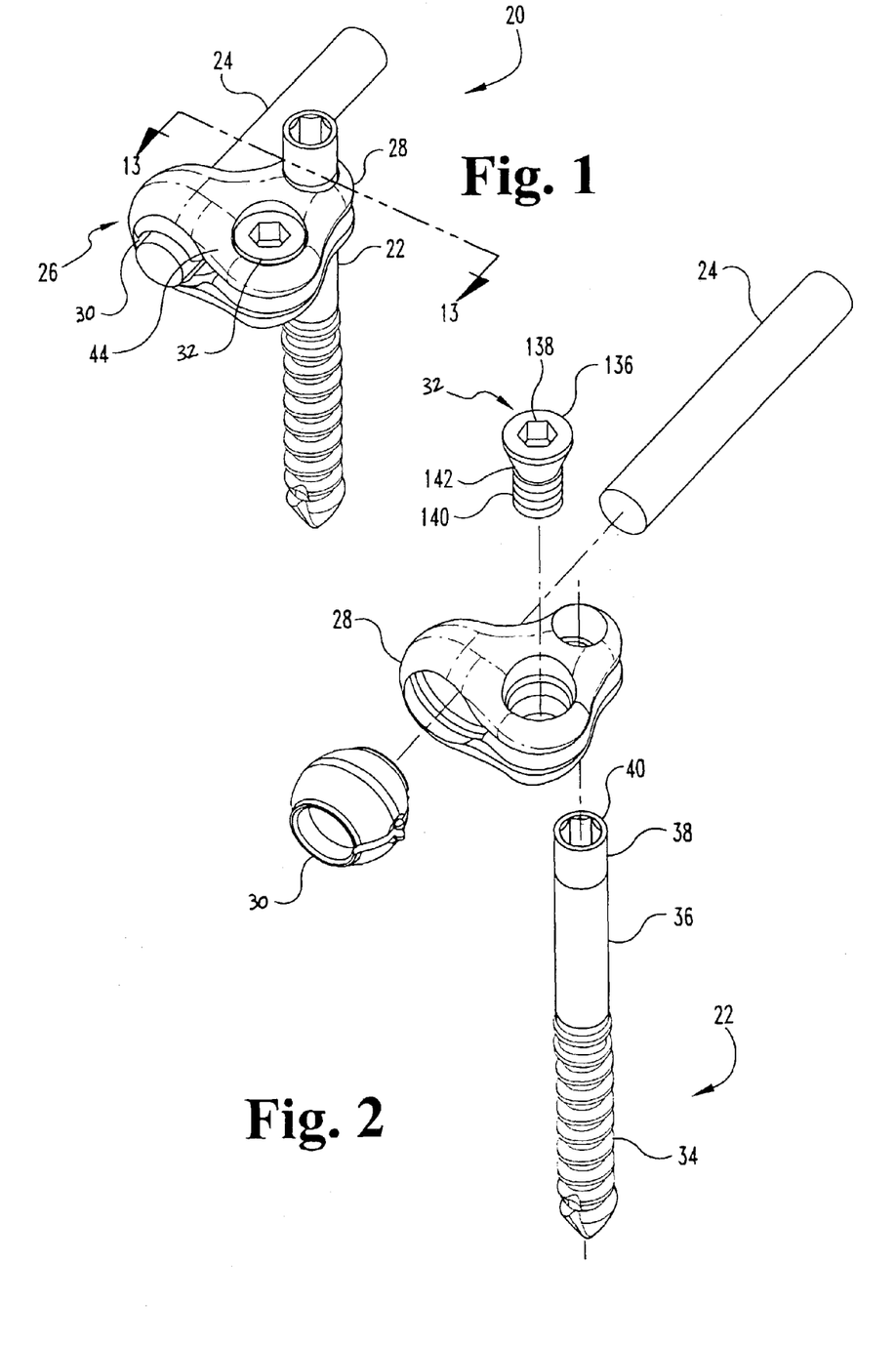
FIG. 1 is a perspective view of one embodiment of an apparatus according to the present invention.
FIG. 2 is an exploded perspective view of the embodiment shown in FIG. 1.

Pedicle screw 22 includes a threaded portion 34, adapted for insertion into a vertebral body (not shown), and a shaft portion 36. In the illustrated embodiment, shaft portion 36 is substantially cylindrical (i.e. substantially a constant diameter) along its entire length, and is relatively smooth and free of protrusions, ridges, or other obstructions. It will be appreciated that shaft portion 36 could have a cross-section other than the circle of a cylindrical shaft, for example a regular hexagonal or similar cross-section, or a roughened surface. Further, other anchoring portions such as a hook may be used in place of threaded portion 34, or hooked members could be used along with threaded embodiments such as pedicle screw 22. Although the term "pedicle screw" is principally used herein, it will be appreciated that element 22 can be threaded, hooked or otherwise configured to engage a bone, and may be configured for attachment to other bones or bone parts. The illustrated embodiment of pedicle screw 22 also includes an upper portion 38 adapted to engage a driving tool to facilitate insertion of pedicle screw 22 into the spine or other bone. In a particular embodiment, upper portion 38 includes an internal hexagonal print 40.

Referring now generally to FIGS. 4-7, there is shown an embodiment of body member 28 of locking assembly 26. In this embodiment, body member 28 is a one-piece member split along a substantially horizontal plane. Body member 28 has an upper portion 42 with an upper surface 44 and a lower portion 46. Portions 42 and 46 are linked by a connecting portion 48 and separated by a medial slot 50. Body member 28 further includes a first side 47 and a second side 49. In this embodiment, body member 28 may be thought of as substantially L-shaped.

A first aperture 52 and a second aperture 54 extend through body member 28 and slot 50. In a particular embodiment, apertures 52 and 54 have axes that are substantially parallel. An upper portion 56 of aperture 52 is within upper portion 42 of body member 28, and a lower portion 58 of aperture 52 is within lower portion 46 of body member 28. An upper portion 60 of aperture 54 is within upper portion 42 of body member 28, and a lower portion 62 of aperture 54 is within lower portion 46 of body member 28. Upper aperture portion 56 is coaxial with lower aperture portion 58 (FIG. 7) and upper aperture portion 60 is coaxial with lower aperture portion 62.

Each aperture portion 56, 58, 60 and 62 includes an upper edge, a lower edge and an interior surface. Thus, with respect to aperture 52, upper aperture portion 56 has an upper edge 64, a lower edge 66 and an interior surface 68, and lower aperture portion 58 has an upper edge 70, a lower edge 72 and an interior surface 74. Interior surfaces 68 and 74 are smooth and have a substantially constant diameter in one embodiment, or alternatively may be roughened such as with knurling or other surface types or treatments. Similarly, with respect to aperture 54, upper aperture portion 60 has an upper edge 76, a lower edge 78 and an interior surface 80, and lower aperture portion 62 has an upper edge 82, a lower edge 84 and an interior surface 86. Interior surface 80 is smooth and has a substantially constant diameter in one embodiment. Upper aperture portion 60 may also include a beveled or rounded portion 88. Where set screw 32 is the member that compresses body member 28 (as described further below), interior surface 86 is threaded.

Figure 7:
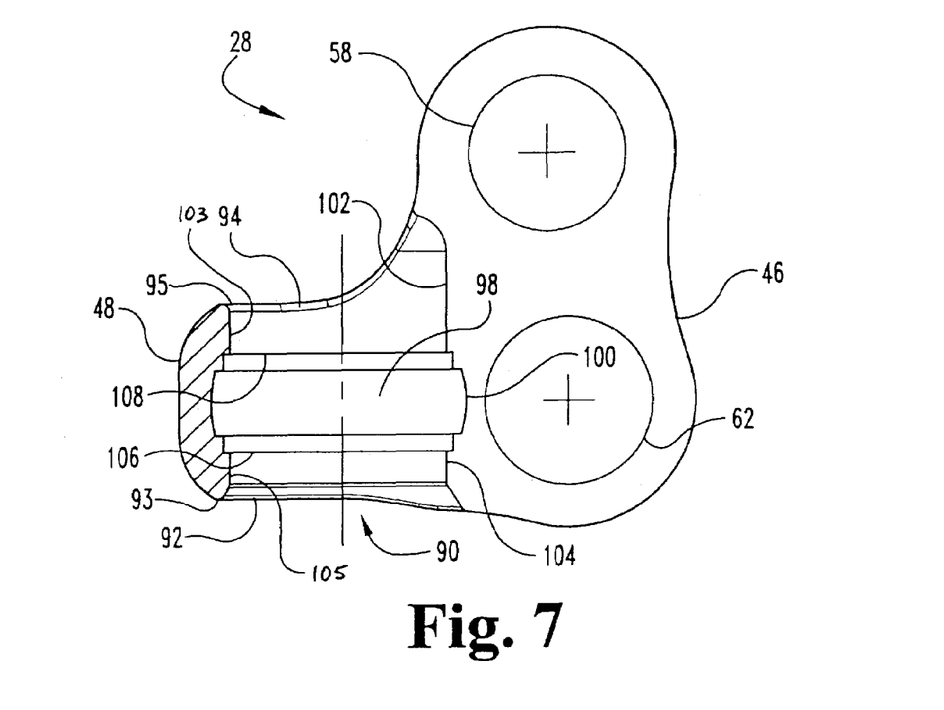
FIG. 7 is a cross-sectional view taken along line 7-7 in FIG. 4, and viewed in the direction of the arrows.

Body element 28 further includes an interior cavity 90. Cavity 90 is open to sides 47 and 49 of body element 28, forming a pair of coaxial openings 92 and 94 (FIG. 7). Opening 92 has an outer edge 93 and opening 94 has an outer edge 95. In a specific embodiment, the axis of openings 92 and 94 is substantially perpendicular to the axis of aperture 52 (i.e., upper aperture portion 56 and lower aperture portion 58) and/or the axis of aperture 54 (i.e. upper aperture portion 60 and lower aperture portion 62). Openings 92 and 94 may have a substantially constant diameter which is greater than rod 24. Alternatively, the outer edges 93 and 95 of openings 92 and 94 may be chamfered so as to allow increased angular positioning of rod 24 passing therethrough, as will be further described below.

With particular reference to FIG. 7, cavity 90 in one embodiment preferably includes a central portion 98, at least a part of which is bounded by an arcuate (e.g., concave) wall portion 100, and also includes substantially cylindrical lateral portions 102 and 104 on each side. Lateral portion 102 includes a wall 103 and lateral portion 104 includes a wall 105. Lateral portions 102 and 104 have a smaller radius than central portion 98 and all three portions are coaxial, in this particular embodiment. Between central portion 98 and each cylindrical lateral portion 102 and 104 are edge surfaces 106 and 108.

Figure 8:
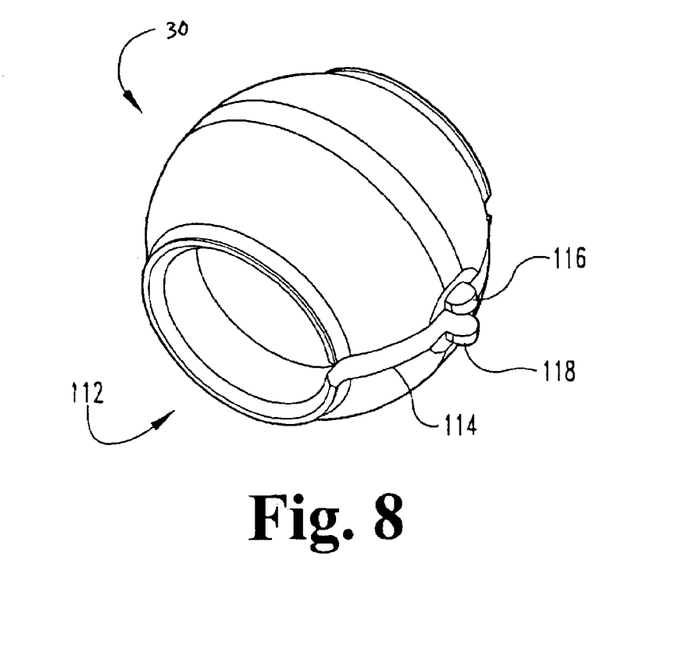
FIG. 8 is a perspective view of the embodiment of a compressible ring shown in FIG. 1.
Figure 9:
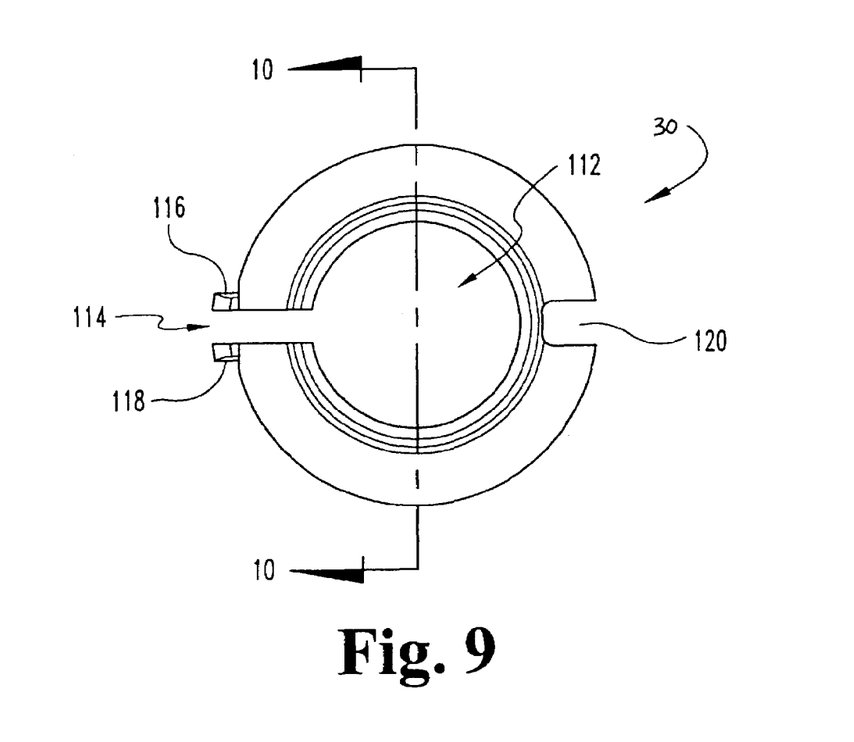
FIG. 9 is an end view of the embodiment shown in FIG. 8.
Figure 10:
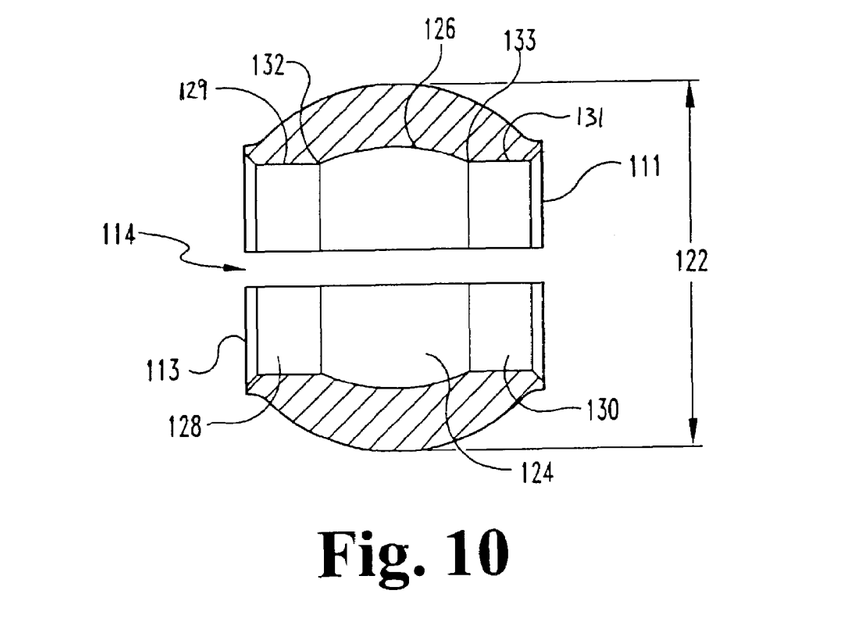
FIG. 10 is a cross-sectional view taken along line 10-10 in FIG. 9, and viewed in the direction of the arrows.

FIGS. 8-10 show an embodiment of compressible ring 30. Ring 30 includes a substantially centrally located passage 112, forming coaxial openings 111 and 113, and a longitudinal slot 114. Preferably, ring 30 includes a first protrusion 116 and a second protrusion 118 adjacent to slot 114. Alternatively, ring 30 could include a single protrusion adjacent to slot 114. Central passage 112 is sized so as to allow rod 24 to pass therethrough, and be movable translationally and rotationally with respect to ring 30, when ring 30 is in the uncompressed state. Slot 114 allows compression of ring 30 so as to lock rod 24 in ring 30 as further described below. Optionally, ring 30 can include a surface groove 120 opposite slot 114, as shown in FIG. 9, to render ring 30 more bendable and improve compression of ring 30. The uncompressed outer diameter 122 of ring 30 is selected such that it is less than interior diameter 91 of uncompressed cavity 90, but greater than the interior diameter 91 of cavity 90 when body element 28 is in the compressed state. This relationship between the uncompressed diameters of ring 30 and cavity 90 allows ring 30 to be rotatably orientable relative to cavity 90 prior to compression. In particular, ring 30 can be manipulated during implantation of orthopedic apparatus 20 when ring 30 is disposed within cavity 90, either directly or indirectly by manipulating rod 24 passing through central passage 112 of ring 30, as described further below.

As seen in the embodiment shown in FIG. 10, central passage 112 includes a central portion 124 of at least one arcuate (e.g., concave) internal wall portion 126, and having lateral substantially cylindrical portions 128 and 130 on each side. Lateral portion 128 includes a wall 129 and lateral portion 130 includes a wall 131. Lateral portions 128 and 130 have a smaller radius than central portion 124 and all three portions are coaxial in this particular embodiment. Between central portion 124 and respective lateral portions 128 and 130 are edge surfaces 132 and 133.

Rod 24 is preferably an essentially smooth (e.g. shot-peened) substantially cylindrical member of sufficient diameter and strength to resist the loads and stresses of the spine. It will be appreciated that rod 24 could be threaded or have a regular hexagonal or other polygonal cross-section in other embodiments. Preferably rod 24 can be bent or configured by the surgeon to conform to the treatment or support of the spine desired by the surgeon.

Figure 12:
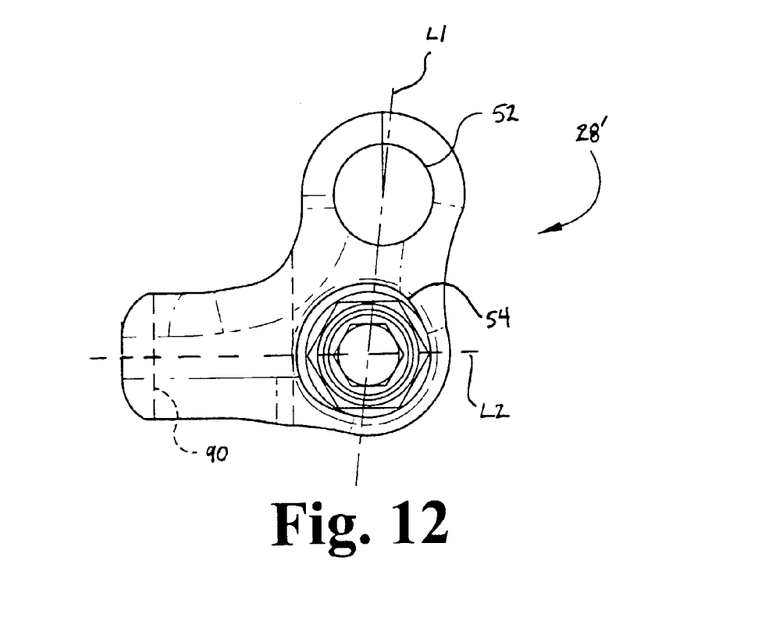
FIG. 12 is a perspective view of a portion of yet another embodiment of an apparatus according to the present invention.

Set screw 32 includes a screw head 136, adapted to engage a driving tool, such as with an internal hexagonal print 138, and a threaded shaft portion 140. Preferably, screw head 136 also includes a beveled or rounded portion 142 which accommodates beveled or rounded portion 88 of upper aperture 60 of body member 28. Optionally, set screw 32 may also include a break away head feature. Examples of set screws having break away portions are shown in U.S. Pat. Nos. 6,193,719 and 6,478,795, which are incorporated herein by reference in their entireties. FIG. 12 shows an alternative embodiment of orthopedic apparatus 20 which includes a set screw 146 having a break away head portion 148.

The use of orthopedic apparatus 20 and its various components will now be described by reference to attaching rod 24 to a portion of the spine (not shown) via pedicle screw 22 and locking assembly 26. It will be appreciated by those of skill in the art that alternative structures and methods may be used, and alternative parts of the body may be instrumented, while remaining within the scope and spirit of the invention.

Figure 13:
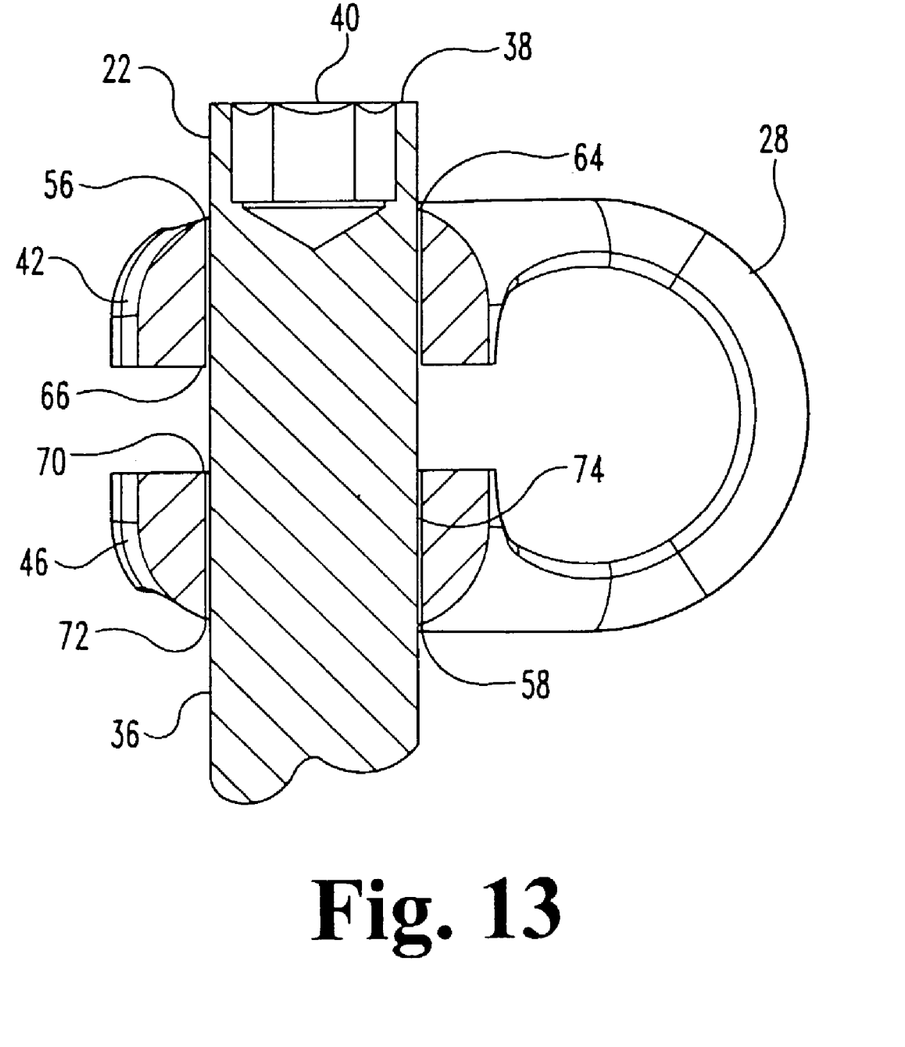
FIG. 13 is a partial cross-sectional view taken along line 13-13 in FIG. 1, and viewed in the direction of the arrows.

A surgical site proximate to the area of the spine to be instrumented is prepared, and a minimally-invasive, open or other incision is made, so as to access the spine. Pedicle screw 22 is inserted into a vertebra via the incision to a desired depth. In one example, pedicle screw 22 is inserted so that the entire length of its threaded portion 34 is within the bone. Body member 28 is placed over screw 22 so that shaft portion 36 of pedicle screw 22 is inserted through aperture 52 (i.e., lower aperture portion 58 and upper aperture portion 56) of body member 28 as shown in FIG. 13. Rod 24 and ring 30 have been removed from this particular view for the sake of clarity. Preferably ring 30 is disposed within cavity 90 of body member 28 prior to insertion of body member 28 into the surgical site and over pedicle screw 22. Alternatively, ring 30 may be inserted into cavity 90 subsequent to positioning of body member 28 on pedicle screw 22.

In this particular example, shaft portion 36 is free of protrusions, ridges, or other obstructions so as to allow body element 28 to be positioned at any point along shaft portion 36 as desired. Preferably, body element 28 is positioned along shaft 36 such that body element 28 does not contact vertebral tissue so as not to damage such tissue. Once body element 28 is positioned on pedicle screw 22, rod 24 is inserted into body member 28 and ring 30 so that rod 24 extends through central passage 112. Rod 24 and ring 30 are manipulated by the surgeon until rod 24 is at the desired angle relative to pedicle screw 22. This maneuverability provides the opportunity to vary the distance between the nearest points of rod 24 and pedicle screw 22, as well as to vary the angle of rod 24 with respect to body member 28 and pedicle screw 22. Alternatively, rod 24 can be inserted through central passage 112 of ring 30 and cavity 90 of body member 28 prior to insertion of pedicle screw 22 through aperture 52 (i.e., upper aperture portion 56 and lower aperture portion 58) of body member 28.

Figure 3:
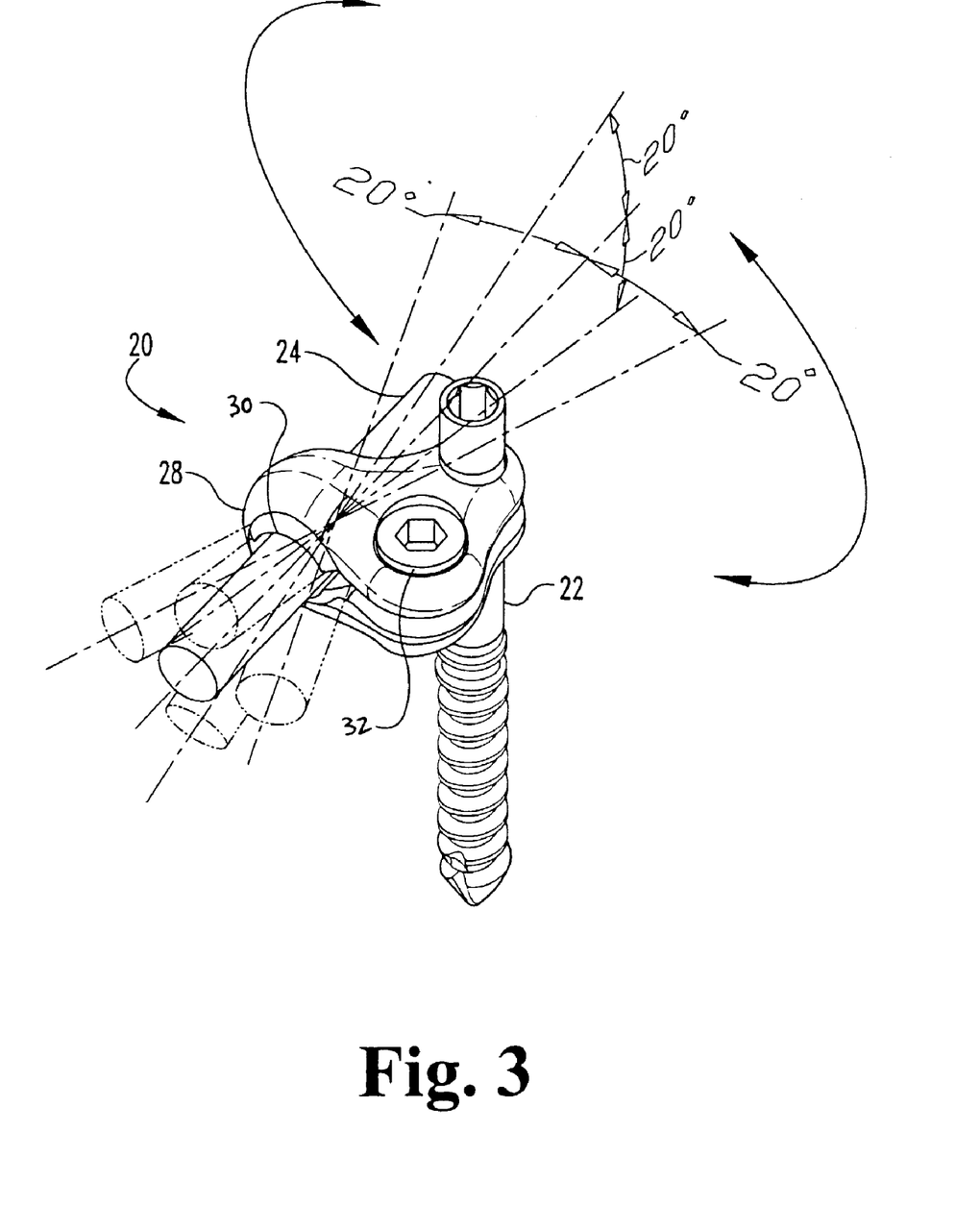
FIG. 3 is a further perspective view of the embodiment shown in FIG. 1.
Figures 4, 5:
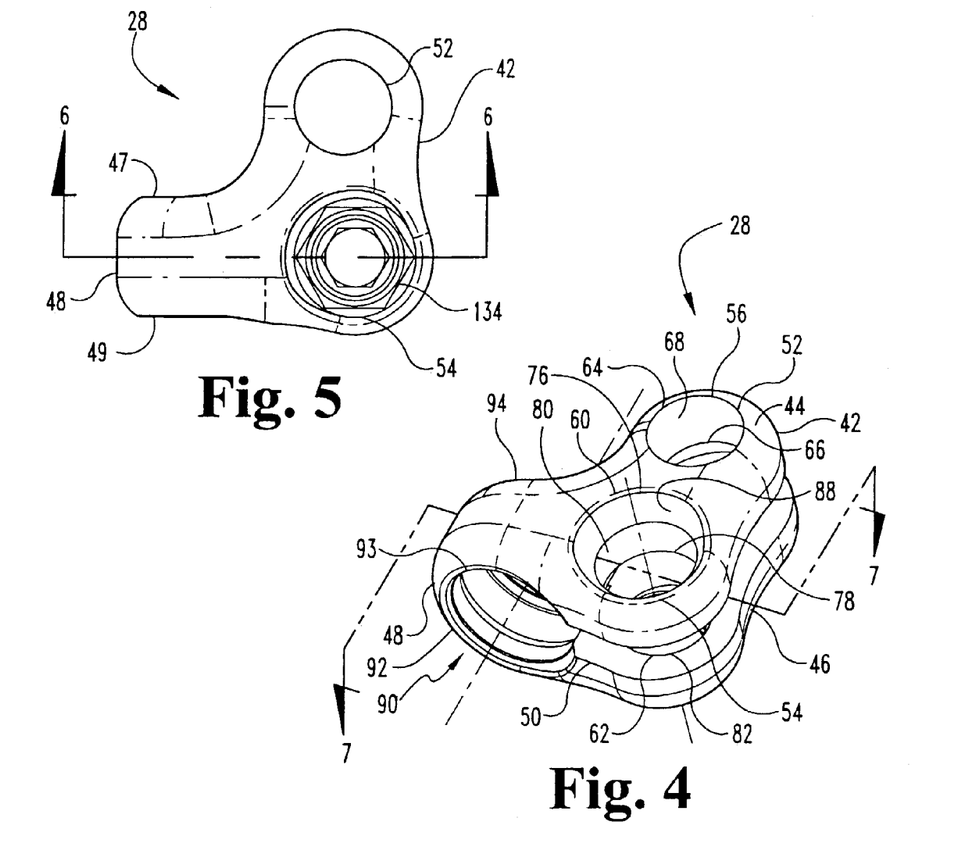
FIG. 4 is a perspective view of the embodiment of a body member shown in FIG. 1.
FIG. 5 is a top view of the embodiment shown in FIG. 4.
Figure 6:
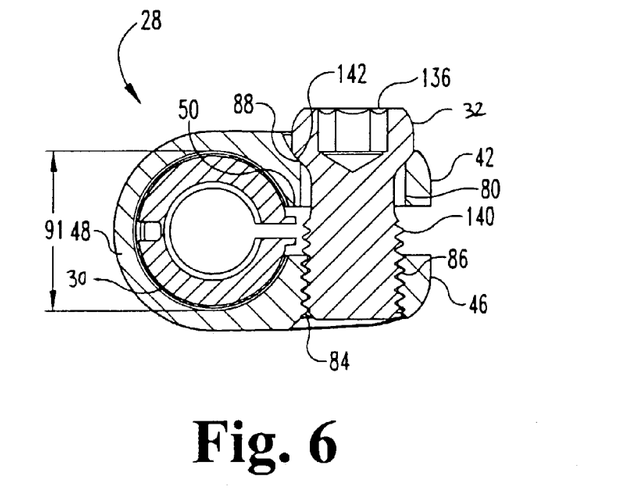
FIG. 6 is a cross-sectional view taken along line 6-6 in FIG. 5, and viewed in the direction of the arrows.

If present, protrusions 116 and 118 on ring 30 as shown in FIG. 6 keep slot 114 substantially aligned with slot 50, e.g. by limiting rotation of ring 30 about the longitudinal axis of central passage 112. It has been found that said alignment can allow more complete or efficient compression of ring 30 than if slot 114 and slot 50 are not aligned. As shown in FIG. 3, rod 24 passing through ring 30 disposed in cavity 90 can have an angle of up to at least 20° with respect to the axis of cavity 90 in each direction. Such angulation allows the surgeon to adjust the position of rod 24 relative to pedicle screw 22 as desired.

Once assembled and positioned as desired, orthopedic apparatus 20 is locked into position. Set screw 32 is inserted into aperture 54 through upper aperture portion 60 and threaded into lower aperture 62 as indicated in FIG. 6. Tightening set screw 32 draws upper portion 42 and lower portion 46 of body member 28 toward one another so as to compress body member 28.

When body member 28 is compressed through the tightening of set screw 32, edges 64 and 66 of upper aperture 56 and edges 70 and 72 of lower aperture 58 pivot along with upper portion 42 and lower portion 46 of body member 28. Edges 66 and 68 are forced into contact with or impinge on shaft portion 36, locking body element 28 to shaft 36 of pedicle screw 22. As body element 28 is compressed (i.e., upper portion 42 and lower portion 46 are forced together), cavity 90 is also compressed. Ring 110 is compressed by walls 100, 101 and 103 of cavity 90 and locking of ring 70 against rotation and translation is assured by edges 106 and 108. As ring 110 is compressed, central passage 112 is also compressed. Walls 125, 126 and 127 of ring 110 are forced against rod 24 to hold rod 24, and edges 132 and 133 lock of the orientation of rod 24 relative to pedicle screw 22.

Figure 11:
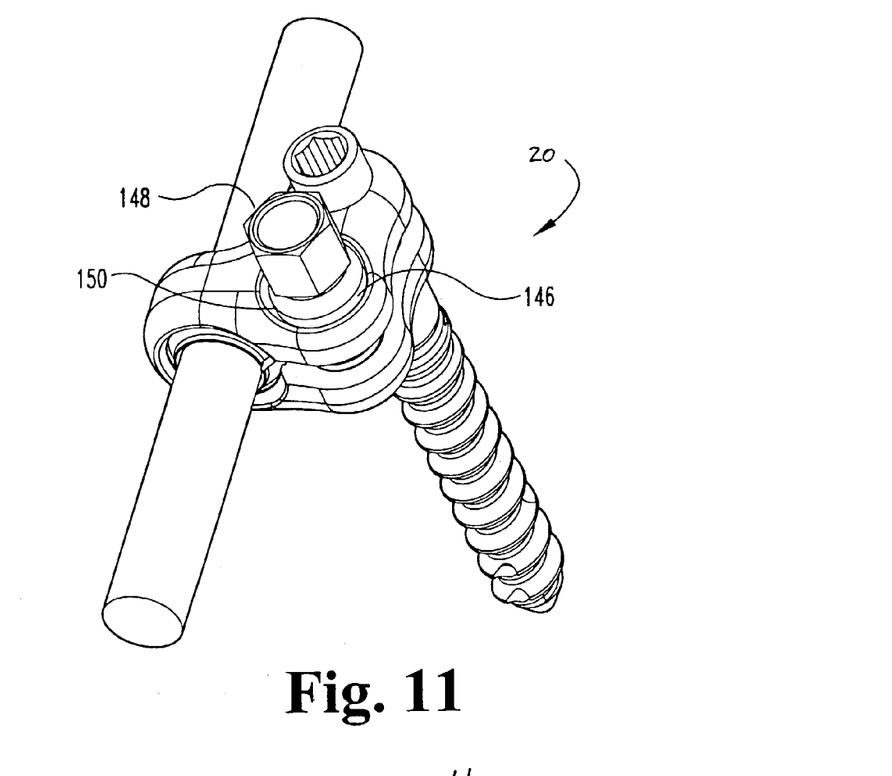
FIG. 11 is a perspective view of another embodiment of an apparatus according to the present invention.

Preferably, once the components of orthopedic apparatus 20 are locked into the desired orientation, head 136 of set screw 32 is flush or below upper surface 44 of body member 28 as shown in FIG. 1. As noted above, apparatus 20 can include a set screw 146 (FIG. 11) having a break away head portion 148. Preferably, once break away head portion 148 is removed from set screw 146, the remaining portion 150 of set screw 148 is flush or below the upper surface of body member 144.

Another embodiment of a body member 28', which may also be thought of as substantially L-shaped, is shown in FIG. 12. Body member 28' is substantially the same as body member 28, described above, with the exception that aperture 52 (for accommodating pedicle screw 22) is positioned further away from the axis of cavity 90. Note in FIG. 12 that a line L1 connecting the axes of apertures 52 and 54 forms an obtuse angle with a line L2 perpendicular to the axis of cavity 90. Such a change allows increased distance between pedicle screw 22 and rod 24 for larger patients or for cases in which additional room and/or different angles between the components of apparatus 20 are indicated.

The components of the assembly are made of a biocompatible material for surgical implantation such as stainless steel, various titanium alloys, appropriate hard plastics or other known materials.

While the invention has been illustrated and described in detail in the drawings and foregoing description, the same is to be considered as illustrative and not restrictive in character, it being understood that only the preferred embodiment has been shown and described and that all changes, modifications and equivalents that come within the spirit of the inventions disclosed are desired to be protected. For example, rod 24 may be connected to ring 30 and body member 28 prior to placement of body member 28 on pedicle screw 22 in the surgical site. In this case, one or more body members 28, each having a ring 30 inserted therein, can be pre-placed on rod 24. After one or more pedicle screws 22 are inserted into bone, rod 24 with pre-placed body member(s) 28 and ring(s) 30 can be placed so that body member(s) 28 are on pedicle screw(s) 22, as described above.

The articles "a", "an", "said" and "the" are not limited to a singular element, and include one or more such elements.

What is claimed is:

1. A orthopedic apparatus comprising:
a bone anchor member having an anchoring portion and a shaft portion;
a longitudinal member;

a locking assembly having a body member and a compressible ring, said assembly connecting said bone anchor member and said longitudinal member; and a set screw threaded into said body member;

wherein said body member includes a lower portion and an upper portion linked by a connecting portion and separated by a slot, said lower portion and said upper portion each including a first aperture and a second aperture, said first aperture being configured such that said shaft portion of said bone anchor member can be passed therethrough, said second aperture being configured such that said set screw can be inserted therein so as to compress said body member, said body member further including a cavity for accommodating said ring and a portion of said longitudinal member;

wherein said compressible ring includes a central passage to receive a portion of said longitudinal member, and wherein compression of said body member by said set screw locks said ring and longitudinal member in a desired position relative to said body member, and said bone anchor member relative to said body member.

2. The orthopedic apparatus of claim 1 wherein said first aperture is smooth-walled.

3. The orthopedic apparatus of claim 1 wherein said bone anchor member is a pedicle screw.

4. The orthopedic apparatus of claim 1 wherein said longitudinal member is a spinal rod.

5. The orthopedic apparatus of claim 1 wherein said set screw includes a break-away head portion.

6. The orthopedic apparatus of claim 1 wherein said compressible ring further includes a longitudinal slot 7. The orthopedic apparatus of claim 6 wherein said compressible ring further includes a groove opposite said longitudinal slot about the axis of said compressible ring.

8. The orthopedic apparatus of claim 6 wherein said compressible ring further includes at least one protrusion adjacent to said longitudinal slot.

9. The orthopedic apparatus of claim 8 wherein said compressible ring further includes two protrusions adjacent to said longitudinal slot.

10. The orthopedic apparatus of claim 6 wherein said central passage further includes a wall portion having at least one edge surface.

11. The apparatus of claim 1, wherein said anchoring portion of said bone anchor member is a threaded portion, and said shaft portion has a top end at one end of said bone anchor member and a bottom end immediately adjacent said threaded portion, and said shaft portion has a substantially constant diameter.

12. The apparatus of claim 1, wherein said second aperture is threaded.

13. An orthopedic apparatus, comprising:

a bone anchor member having an anchoring portion and a shaft portion;

a longitudinal member;

a locking assembly having a substantially L-shaped body member and a compressible ring, said assembly connecting said bone anchor member and said longitudinal member; and a set screw connected to said body member;

wherein said body member includes a first aperture being configured such that said shaft portion of said bone anchor member can be passed therethrough and a second aperture being configured such that said set screw can be inserted therein so as to compress said body member, said body member further including a cavity for accommodating said ring and a portion of said longitudinal member;

wherein said compressible ring includes a central passage to receive a portion of said longitudinal member, and wherein compression of said body member by said set screw locks said ring and longitudinal member in a desired position relative to said body member and said bone anchor member relative to said body member.

14. The apparatus of claim 13, wherein said ring includes an exterior groove.

15. The apparatus of claim 13 wherein said bone anchor member is a pedicle screw.

16. The apparatus of claim 13 wherein said set screw includes a break-away head portion.

17. The apparatus of claim 13 wherein said compressible ring includes a longitudinal slot.

18. The apparatus of claim 17 wherein said compressible ring includes at least one protrusion substantially parallel to said longitudinal slot.

19. The apparatus of claim 17 wherein said compressible ring includes first and second protrusions substantially parallel to said longitudinal slot, said protrusions substantially facing each other across said slot.

20. The apparatus of claim 17 wherein said compressible ring further includes an external groove opposite said longitudinal slot.

21. The apparatus of claim 13, wherein said anchoring portion of said bone anchor member is a threaded portion, and said shaft portion has a top end at one end of said bone anchor member and a bottom end immediately adjacent said threaded portion, and said shaft portion has a substantially constant diameter.

22. The apparatus of claim 13, wherein said second aperture is threaded.

23. An orthopedic apparatus, comprising:

a bone anchor member having an anchoring portion and a shaft portion;

a longitudinal member;

a locking assembly having a substantially L-shaped body member and a compressible ring, said assembly connecting said bone anchor member and said longitudinal member; and a set screw connected to said body member;

wherein said body member includes a first aperture being configured such that said shaft portion of said bone anchor member can be passed therethrough and a second aperture being configured such that said set screw can be inserted therein so as to compress said body member, said body member further including a cavity for accommodating said ring and a portion of said longitudinal member;

wherein said compressible ring includes a central passage to receive a portion of said longitudinal member;

wherein compression of said body member by said set screw locks said ring and longitudinal member in a desired position relative to said body member and said bone anchor member relative to said body member; and wherein said substantially L-shaped body member has a first end portion, a second end portion, and a corner portion, said cavity being in or adjacent said first end portion, said first aperture being in or adjacent said second end portion, and said second aperture being in said corner portion.

24. An orthopedic apparatus, comprising:

a bone anchor member having a shaft portion and a bone connecting portion, a longitudinal support member;

a clamp having a medial slot, a first aperture for accommodating said bone anchor member, a second aperture, and a cavity transverse to said first aperture and offset from a line connecting said apertures, said clamp having an uncompressed state and a compressed state in which said cavity is radially smaller than when said clamp is in said uncompressed state;

a split ring surrounding a portion of said longitudinal support member, said split ring having an uncompressed state and a compressed state, said split ring being within said cavity of said clamp and being rotationally movable with respect to said clamp when said clamp is in said uncompressed state; and a set screw inserted in said second aperture of said clamp, said set screw providing a force resulting in changing said clamp from said uncompressed state to said compressed state, thereby compressing said split ring and securing said split ring and said longitudinal member against movement with respect to each other and with respect to said clamp, wherein said first aperture is closer to said longitudinal member than said second aperture.

25. The apparatus of claim 24, wherein said clamp in said uncompressed state is movable with respect to said bone anchor member, and said clamp in said compressed state contacts said shaft portion of said bone anchor member to secure said clamp and said bone anchor member with respect to each other.

26. The apparatus of claim 25, wherein said bone connecting portion of said bone anchor member is a threaded portion, and said shaft portion has a top end and a bottom end immediately adjacent said threaded portion, and said shaft portion has a substantially constant diameter.

27. The apparatus of claim 24, wherein said ring includes a substantially longitudinal slot.

28. The apparatus of claim 27, wherein said ring includes a substantially longitudinal groove approximately diametrically opposite said longitudinal slot.

29. The apparatus of claim 27, wherein said ring has a longitudinal axis and includes at least one protrusion adjacent said longitudinal slot, said protrusion limiting rotation of said ring around said longitudinal axis with respect to said clamp.

30. The apparatus of claim 24, wherein said set screw includes a break-away head portion.

31. The apparatus of claim 24, wherein said longitudinal member is a spinal rod.

32. The apparatus of claim 24, wherein only one bone anchor member is connected to said clamp.

33. An orthopedic apparatus, comprising:

a bone anchor member having a shaft portion and a bone connecting portion;

a longitudinal support member;

a clamp having a medial slot, a first aperture for accommodating said bone anchor member, a second aperture, and a cavity transverse to said first aperture and offset from a line connecting said apertures, said clamp having an uncompressed state and a compressed state in which said cavity is radially smaller than when said clamp is in said uncompressed state;

a split ring surrounding a portion of said longitudinal support member, said split ring having an uncompressed state and a compressed state, said split ring being within said cavity of said clamp and being rotationally movable with respect to said clamp when said clamp is in said uncompressed state; and a set screw inserted in said second aperture of said clamp, said set screw providing a force resulting in changing said clamp from said uncompressed state to said compressed state, thereby compressing said split ring and securing said split ring and said longitudinal member against movement with respect to each other and with respect to said clamp, wherein said second aperture is closer to said longitudinal member than said first aperture.

34. The apparatus of claim 33, wherein said clamp in said uncompressed state is movable with respect to said bone anchor member, and said clamp in said compressed state contacts said shaft portion of said bone anchor member to secure said clamp and said bone anchor member with respect to each other.

35. The apparatus of claim 34, wherein said bone connecting portion of said bone anchor member is a threaded portion, and said shaft portion has a top end and a bottom end immediately adjacent said threaded portion, and said shaft portion has a substantially constant diameter.

36. The apparatus of claim 33, wherein said ring includes a substantially longitudinal slot.

37. The apparatus of claim 36, wherein said ring includes a substantially longitudinal groove approximately diametrically opposite said longitudinal slot.

38. The apparatus of claim 36, wherein said ring has a longitudinal axis and includes at least one protrusion adjacent said longitudinal slot, said protrusion limiting rotation of said ring around said longitudinal axis with respect to said clamp.

39. The apparatus of claim 33, wherein said set screw includes a break-away head portion.

40. The apparatus of claim 33, wherein said longitudinal member is a spinal rod.

41. The apparatus of claim 33, wherein only one bone anchor member is connected to said clamp.

* * * * *